US008399517B2

(12) United States Patent
Marquis et al.

(10) Patent No.: US 8,399,517 B2
(45) Date of Patent: Mar. 19, 2013

(54) CALCILYTIC COMPOUNDS

(75) Inventors: Robert W. Marquis, Collegeville, PA (US); Linda N. Casillas, Collegeville, PA (US); Joshi M. Ramanjulu, Collegeville, PA (US); James Francis Callahan, King of Prussia, PA (US)

(73) Assignee: GlaxoSmithKline, LLC, Philadelphia, PA (US)

( * ) Notice: Subject to any disclaimer, the term of this patent is extended or adjusted under 35 U.S.C. 154(b) by 0 days.

(21) Appl. No.: 12/894,644

(22) Filed: Sep. 30, 2010

(65) Prior Publication Data

US 2011/0054021 A1 Mar. 3, 2011

Related U.S. Application Data

(60) Continuation of application No. 12/393,284, filed on Feb. 26, 2009, now Pat. No. 7,829,594, which is a division of application No. 10/536,416, filed as application No. PCT/US03/37461 on Nov. 25, 2003, now Pat. No. 7,514,473.

(60) Provisional application No. 60/429,105, filed on Nov. 26, 2002.

(51) Int. Cl.
*A61K 31/195* (2006.01)
*C07C 229/00* (2006.01)

(52) U.S. Cl. ........................................ 514/567; 562/442
(58) Field of Classification Search .................. 514/567; 562/442

See application file for complete search history.

(56) References Cited

U.S. PATENT DOCUMENTS

| | | | | |
|---|---|---|---|---|
| 4,212,877 A | 7/1980 | Köppe et al. | ................... | 424/273 |
| 4,229,449 A | 10/1980 | Melloni et al. | ........... | 424/248.58 |
| 4,234,595 A | 11/1980 | Kreighbaum et al. | ......... | 424/274 |
| 4,255,430 A | 3/1981 | Köppe et al. | ................... | 424/258 |
| 4,256,756 A | 3/1981 | Köppe et al. | ................... | 424/273 |
| 4,381,309 A | 4/1983 | Köppe et al. | ............. | 424/273 B |
| 4,495,352 A | 1/1985 | Kreighbaum et al. | ......... | 544/284 |
| 4,767,784 A | 8/1988 | Zölss et al. | .................... | 514/554 |
| 4,806,655 A | 2/1989 | Wagnon et al. | ................ | 548/455 |
| 6,022,894 A | 2/2000 | Delmar et al. | ................ | 514/524 |
| 6,291,459 B1 | 9/2001 | Bhatnagar et al. | ......... | 514/237.8 |
| 6,294,531 B1 | 9/2001 | Barmore et al. | ........... | 514/227.5 |
| 6,335,338 B1 | 1/2002 | Bhatnagar et al. | ......... | 514/239.2 |
| 6,395,919 B1 | 5/2002 | Bhatnagar et al. | ............ | 558/414 |
| 6,417,215 B1 | 7/2002 | Lago | ............. | 514/381 |
| 6,432,656 B1 | 8/2002 | Del Mar et al. | ............. | 435/7.21 |
| 6,521,667 B1 | 2/2003 | Del Mar et al. | ............. | 514/653 |
| 6,818,660 B2 | 11/2004 | Del Mar et al. | ............. | 514/357 |
| 6,864,267 B2 | 3/2005 | Bhatnagar et al. | ............ | 514/336 |
| 6,890,955 B2 | 5/2005 | Hadri et al. | .................... | 514/567 |
| 7,109,238 B2 * | 9/2006 | Lago et al. | .................... | 514/475 |
| 7,202,261 B2 | 4/2007 | Del Mar et al. | ............. | 514/357 |
| 7,514,473 B2 | 4/2009 | Marquis et al. | ............. | 514/567 |
| 7,829,594 B2 * | 11/2010 | Marquis et al. | ............. | 514/567 |
| 2002/0019440 A1 | 2/2002 | Philippe et al. | ............... | 514/466 |
| 2007/0010571 A1 | 1/2007 | Garvey et al. | ................. | 514/419 |
| 2007/0197555 A1 | 8/2007 | Shcherbakova et al. | ... | 514/259.1 |
| 2007/0203226 A1 | 8/2007 | Marquis | ........................ | 514/444 |
| 2008/0234370 A1 | 9/2008 | Marquis et al. | ............... | 514/532 |
| 2009/0163589 A1 | 6/2009 | Marquis et al. | ............... | 514/539 |

FOREIGN PATENT DOCUMENTS

| | | |
|---|---|---|
| DE | 4040186 | 6/1991 |
| DE | 298506 | 2/1992 |
| ES | 442062 | 4/1977 |
| ES | 480066 | 4/1980 |
| ES | 421076 | 4/1986 |
| GB | 20149681 A | 9/1979 |
| WO | WO 97/31640 | 9/1997 |
| WO | WO 97/37967 | 10/1997 |
| WO | WO 98/44925 | 10/1998 |
| WO | WO 99/51241 | 10/1999 |
| WO | WO 01/07026 A2 | 2/2001 |
| WO | WO01/08673 * | 2/2001 |
| WO | WO 01/08673 A1 | 2/2001 |
| WO | WO 01/53254 | 7/2001 |
| WO | WO 02/07673 A2 | 1/2002 |
| WO | WO 02/34204 A2 | 5/2002 |
| WO | WO 02/38106 A2 | 5/2002 |
| WO | WO 02/072760 A2 | 9/2002 |
| WO | WO 02/07673 A3 | 10/2003 |
| WO | WO 2005/030746 A1 | 4/2005 |
| WO | WO 2005/077802 A1 | 8/2005 |
| WO | WO 2006/052899 A2 | 5/2006 |
| WO | WO 2006/078995 A1 | 7/2006 |

OTHER PUBLICATIONS

Abstract 91-194494/27 (Derwent Information Ltd.) Geisen et al. Use of 3-amino-propan-1,2-di:ol derivatives as racemate, Enantiomeric mixture of pure enantiomer in treatment of diabetes mellitus. German Patent DE 40 40 186 A1. Jun. 27, 1991.
B. Law and L. Stafford. Journal of Pharmaceutical & Biomedical Analysis. vol. II, No. 8, pp. 729-736 (1993).
CA Abstract DN 117:7640 Bercher, H. and Grisk, S. (to Ernst-Moritz-Arndt Univ.) Process for the preparation of 1-(dihalophenoxy)-3-[(1,1-dimethyl-2-phenylethyl)amino]-2-propanols and their use as β-adrenergic agaonists or antagonists. German (DDR) Patent 298506. Feb. 27, 1992.
CA Abstract DN 85:142815 Dr. Andreu. 1-Aryloxy-3-(aralkylamino)-2-propanols. Spanish Application 421076. Apr. 1, 1986.
CA Abstract DN 88:22352 Dr. Andreu. 1-Aryloxy-2-hydroxy-3-alkylaminopropanes. Spanish Application 442062. Apr. 1, 1977.
CA Abstract DN 93:167911 Montoro, F. et al. [to Especialidades Latinas Medicamentos Universales) 1-(4-Chloro-α,α-dibenzomethylbenzenoethanamino)-2-hydroxy-3-(aryloxy)propanes. Spanish Application 480066. Apr. 1, 1980.
Castedo et al., "Bloqueantes β-Andrenergicos: Sintesis Del (R)-1-[(1,1-Dimetil-2-Feniletil)Amino]-3-(3,4-Dichlorofenox])-2-Propanol", *Anales De Quimica*, vol. 80, No. 3, pp. 291-294 (1984) (Spanish).
F. Espinosa and A. Paniello, Anales De Quimica, vol. 77, No. 1, pp. 22-27 (1981) (Spanish).

(Continued)

*Primary Examiner* — Taylor Victor Oh
(74) *Attorney, Agent, or Firm* — Loretta J. Sauermelch; Alan Scrivner

(57) ABSTRACT

Novel calcilytic compounds and methods of using them are provided.

3 Claims, No Drawings

OTHER PUBLICATIONS

Kreighbaum et al., "Antihypertensive Indole Derivatives of Phenoxypropanolamines with β-Andrenergic Receptor Antagonist and Vasodilating Activity", J. Med. Chem, vol. 23, No. 3, pp. 285-289 (1980).

Shuker et al., "The Application of High-Throughput Synthesis and Purification to the Preparation of Ethanolamines", Tetrahedron Letters, vol. 38, No. 35, pp. 6149-6152 (1997).

* cited by examiner

CALCILYTIC COMPOUNDS

This application is a continuation of U.S. application Ser. No. 12/393,284 filed Feb. 26, 2009, now U.S. Pat. No. 7,829,594 which is a divisional of U.S. application Ser. No. 10/536,416, filed 25 May 2005, now U.S. Pat. No. 7,514,473 which is a 371 application of PCT/US2003/037461 filed 25 Nov. 2003 which claims the benefit of U.S. Provisional Application No. 60/429,105, filed 26 Nov. 2002.

FIELD OF INVENTION

The present invention relates novel compounds able to inhibit calcium receptor activity and the use of such compounds. Preferably, the compounds described herein are administered to patients to achieve a therapeutic effect.

BACKGROUND OF THE INVENTION

The present invention relates to novel calcilytic compounds, pharmaceutical compositions containing these compounds and their use as calcium receptor antagonists.

In mammals, extracellular $Ca^{2+}$ is under rigid homeostatic control and regulates various processes such as blood clotting, nerve and muscle excitability, and proper bone formation. Extracellular $Ca^{2+}$ inhibits the secretion of parathyroid hormone ("PTH") from parathyroid cells, inhibits bone resorption by osteoclasts, and stimulates secretion of calcitonin from C-cells. Calcium receptor proteins enable certain specialized cells to respond to changes in extracellular $Ca^{2+}$ concentration.

PTH is the principal endocrine factor regulating $Ca^{2+}$ homeostasis in the blood and extracellular fluids. PTH, by acting on bone and kidney cells, increases the level of $Ca^{2+}$ in the blood. This increase in extracellular $Ca^{2+}$ then acts as a negative feedback signal, depressing PTH secretion. The reciprocal relationship between extracellular $Ca^{2+}$ and PTH secretion forms an important mechanism maintaining bodily $Ca^{2+}$ homeostasis.

Extracellular $Ca^{2+}$ acts directly on parathyroid cells to regulate PTH secretion. The existence of a parathyroid cell surface protein which detects changes in extracellular $Ca^{2+}$ has been confirmed. See Brown et al., Nature 366:574, 1993. In parathyroid cells, this protein, the calcium receptor, acts as a receptor for extracellular $Ca^{2+}$, detects changes in the ion concentration of extracellular $Ca^{2+}$, and initiates a functional cellular response, PTH secretion.

Extracellular $Ca^{2+}$ influences various cell functions, reviewed in Nemeth et al., Cell Calcium 11:319, 1990. For example, extracellular $Ca^{2+}$ plays a role in parafollicular (C-cells) and parathyroid cells. See Nemeth, Cell Calcium 11:323, 1990. The role of extracellular $Ca^{2+}$ on bone osteoclasts has also been studied. See Zaidi, Bioscience Reports 10:493, 1990.

Various compounds are known to mimic the effects of extra-cellular $Ca^{2+}$ on a calcium receptor molecule. Calcilytics are compounds able to inhibit calcium receptor activity, thereby causing a decrease in one or more calcium receptor activities evoked by extracellular $Ca^{2+}$. Calcilytics are useful as lead molecules in the discovery, development, design, modification and/or construction of useful calcium modulators, which are active at $Ca^{2+}$ receptors. Such calcilytics are useful in the treatment of various disease states characterized by abnormal levels of one or more components, e.g., polypeptides such as hormones, enzymes or growth factors, the expression and/or secretion of which is regulated or affected by activity at one or more $Ca^{2+}$ receptors. Target diseases or disorders for calcilytic compounds include diseases involving abnormal bone and mineral homeostasis.

Abnormal calcium homeostasis is characterized by one or more of the following activities: an abnormal increase or decrease in serum calcium; an abnormal increase or decrease in urinary excretion of calcium; an abnormal increase or decrease in bone calcium levels (for example, as assessed by bone mineral density measurements); an abnormal absorption of dietary calcium; an abnormal increase or decrease in the production and/or release of messengers which affect serum calcium levels such as PTH and calcitonin; and an abnormal change in the response elicited by messengers which affect serum calcium levels.

Thus, calcium receptor antagonists offer a unique approach towards the pharmacotherapy of diseases associated with abnormal bone or mineral homeostasis, such as hypoparathyroidism, osteosarcoma, periodontal disease, fracture healing, osteoarthritis, rheumatoid arthritis, Paget's disease, humoral hypercalcemia associated with malignancy and fracture healing, and osteoporosis.

SUMMARY OF THE INVENTION

The present invention features calcilytic compounds. "Calcilytic compounds" refer to compounds able to inhibit calcium receptor activity. The ability of a compound to "inhibit calcium receptor activity" means that the compound causes a decrease in one or more calcium receptor activities evoked by extracellular $Ca^{2+}$.

The use of calcilytic compounds to inhibit calcium receptor activity and/or achieve a beneficial effect in a patient are described below. Also described below are techniques which can be used to obtain additional calcilytic compounds.

An example of featured calcilytic compounds are Structure I having the chemical formula:

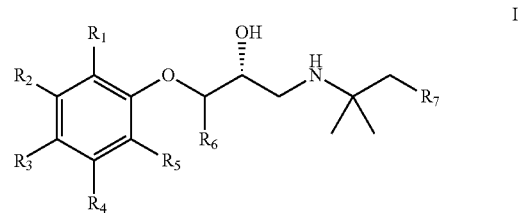

wherein:
$R_1$ and $R_5$ are independently selected from the group consisting of H and halogen
$R_2$, $R_3$ and $R_4$ are independently selected from the group consisting of H, halogen and J-K wherein:
  J is a covalent bond, alkylene or alkenyl: and K is selected from the group of $CO_2R_8$, such that $R_8$ is H or alkyl
$R_6$ is selected from the group consisting of H or alkyl
$R_7$ is selected from the group consisting of aryl or fused aryl, dihydro, tetrahydro fused aryl, heteroaryl, unsubstituted or substituted with any substituent selected from the group consisting of OH, halogen, $C_{1-4\ alkyl}$, $C_{1-4alkoxy}$, $C_{3-6\ cycloalkyl}$, $CF_3$, $OCF_3$, CN and $NO_2$,
and pharmaceutically acceptable salts and complexes thereof.

"Alk" refers to either alkyl or alkenyl. "Lower alk" refers to either lower alkyl or lower alkenyl, preferably lower alkyl.

"Alkenyl" refers to an optionally substituted hydrocarbon group containing at least one carbon-carbon double bond between the carbon atoms and containing 2-6 carbon atoms joined together. The alkenyl hydrocarbon group may be straight-chain. Straight-chain alkenyl preferably has 2 to 4 carbons.

"Alkyl" refers to an optionally substituted hydrocarbon group joined by single carbon-carbon bonds and having 1 to 6 carbon atoms joined together. The alkyl hydrocarbon group may be straight-chain or contain one or more branches. Branched- and straight-chain alkyl preferably have 1 to 4 carbons, each of which may be optionally substituted. Alkyl substituents are each independently selected from the group consisting of: lower alkyl, unsubstituted aryl, OH, $NH_2$, NH-lower alkyl, and N(lower alkyl)$_2$. Preferably, no more than two substituents are present. Even more preferably, alkyl is a lower alkyl which is unsubstituted branched- or straight-chain alkyl having 2 to 4 carbons.

"Aryl" refers to an optionally substituted aromatic group with at least one ring having a conjugated or fused ring systems. Aryl includes carbocyclic aryl, heterocyclic aryl and biaryl groups, all of which may be optionally substituted. Preferably, the aryl is either optionally substituted phenyl or optionally substituted pyridyl.

"Alkoxy" refers to oxygen joined to an unsubstituted alkyl 1 to 4 carbon atoms in length, preferably 1 to 2 carbons in length. More preferably, the alkoxy is methoxy.

Preferred compounds useful in the present invention are selected from the group consisting of:

3-{3,4-Difluoro-5-[(R)-2-hydroxy-3-(2-indan-2-yl-1,1-dimethyl-ethylamino)-propoxy]-phenyl}-acrylic acid hydrochloride;

3-{3,4-Difluoro-5-[(R)-2-hydroxy-3-(2-indan-2-yl-1,1-dimethyl-ethylamino)-propoxy]-phenyl}-propionic acid hydrochloride;

3-{3,4-Difluoro-5-[(R)-2-hydroxy-3-(2-indan-2-yl-1,1-dimethyl-ethylamino)-propoxy]-phenyl}-propionic acid ethyl ester hydrochloride;

(E)-3-{3,4-Difluoro-5-[(R)-2-hydroxy-3-(2-indan-2-yl-1,1-dimethyl-ethylamino)-propoxy]-phenyl}-pent-4-enoic acid hydrochloride;

5-{3,4-Difluoro-5-[(R)-2-hydroxy-3-(2-indan-2-yl-1,1-dimethyl-ethylamino)-propoxy]-phenyl}-pentanoic acid hydrochloride;

5-{3,4-Difluoro-5-[(R)-2-hydroxy-3-(2-indan-2-yl-1,1-dimethyl-ethylamino)-propoxy]-phenyl}-pentanoic acid ethyl ester;

3-{4-Bromo-3-[(R)-2-hydroxy-3-(2-indan-2-yl-1,1-dimethyl-ethylamino)-propoxy]-phenyl}-propionic acid ethyl ester hydrochloride;

3-{4-Bromo-3-[(R)-2-hydroxy-3-(2-indan-2-yl-1,1-dimethyl-ethylamino)-propoxy]-phenyl}-propionic acid hydrochloride;

3-{2,3-Difluoro-4-[(R)-2-hydroxy-3-(2-indan-2-yl-1,1-dimethyl-ethylamino)-propoxy]-phenyl}-propionic acid hydrochloride;

3-{2,3-Difluoro-4-[(R)-2-hydroxy-3-(2-indan-2-yl-1,1-dimethyl-ethylamino)-propoxy]-phenyl}-propionic acid ethyl ester hydrochloride;

(E)-3-{2,3-Dichloro-5-[(R)-2-hydroxy-3-(2-indan-2-yl-1,1-dimethyl-ethylamino)-propoxy]-phenyl}-acrylic acid hydrochloride;

3-{2,3-Chloro-4-[(R)-2-hydroxy-3-(2-indan-2-yl-1,1-dimethyl-ethylamino)-propoxy]-phenyl}-propionic acid hydrochloride;

3-{2,3-Chloro-4-[(R)-2-hydroxy-3-(2-indan-2-yl-1,1-dimethyl-ethylamino)-propoxy]-phenyl}-propionic acid ethyl ester trifluoroacetate;

3-{4-Fluoro-3-[(R)-2-hydroxy-3-(2-indan-2-yl-1,1-dimethyl-ethylamino)-propoxy]-phenyl}-propionic acid ethyl ester hydrochloride;

3-{4-Fluoro-3-[(R)-2-hydroxy-3-(2-indan-2-yl-1,1-dimethyl-ethylamino)-propoxy]-phenyl}-propionic acid hydrochloride;

3-{2-Chloro-5-[(R)-2-hydroxy-3-(2-indan-2-yl-1,1-dimethyl-ethylamino)-propoxy]-phenyl}-propionic acid ethyl ester hydrochloride;

3-{2-Chloro-5-[(R)-2-hydroxy-3-(2-indan-2-yl-1,1-dimethyl-ethylamino)-propoxy]-phenyl}-propionic acid hydrochloride;

3-{2,4-Dichloro-5-[(R)-2-hydroxy-3-(2-indan-2-yl-1,1-dimethyl-ethylamino)-propoxy]-phenyl}-propionic acid ethyl ester;

5-{2,3-Dichloro-4-[(R)-2-hydroxy-3-(2-indan-2-yl-1,1-dimethyl-ethylamino)-propoxy]-phenyl}-pentanoic acid trifluoroacetate;

5-{2,3-Dichloro-4-[(R)-2-hydroxy-3-(2-indan-2-yl-1,1-dimethyl-ethylamino)-propoxy]-phenyl}-pentanoic acid ethyl ester trifluoroacetate;

3-{2,3-Dichloro-4-[2-(R)-hydroxy-3-(2-indan-2-yl-1,1-dimethyl-ethylamino)-1(R)-methyl-propoxy]-phenyl propionic acid ethyl ester hydrochloride;

3-{2,3-Dichloro-4-[2-(S)-hydroxy-3-(2-indan-2-yl-1,1-dimethyl-ethyl amino)-1(S)-methyl-propoxy]-phenyl propionic acid ethyl ester hydrochloride;

3-{2,3-Dichloro-4-[2-(R)-hydroxy-3-(2-indan-2-yl-1,1-dimethyl-ethyl amino)-1(S)-methyl-propoxy]-phenyl propionic acid ethyl ester hydrochloride;

3-{2,3-Dichloro-4-[2-(S)-hydroxy-3-(2-indan-2-yl-1,1-dimethyl-ethyl amino)-1(R)-methyl-propoxy]-phenyl propionic acid ethyl ester hydrochloride;

3-{2,3-Dichloro-4-[2-(R)-hydroxy-3-(2-indan-2-yl-1,1-dimethyl-ethyl amino)-1(R)-methyl-propoxy]-phenyl propionic acid hydrochloride;

3-{2,3-Dichloro-4-[2-(S)-hydroxy-3-(2-indan-2-yl-1,1-dimethyl-ethyl amino)-1(S)-methyl-propoxy]-phenyl propionic acid hydrochloride;

3-{2,3-Dichloro-4-[2 (-R)-hydroxy-3-(2-indan-2-yl-1,1-dimethyl-ethyl amino)-1(S)-methyl-propoxy]-phenyl propionic acid hydrochloride;

3-{2,3-Dichloro-4-[2-(S)-hydroxy-3-(2-indan-2-yl-1,1-dimethyl-ethyl amino)-1(R)-methyl-propoxy]-phenyl propionic acid hydrochloride;

3-{3-Chloro-4-[(R)-2-hydroxy-3-(2-indan-2-yl-1,1-dimethyl-ethylamino)-propoxy]-phenyl}-propionic acid ethyl ester;

3-{3-Chloro-4-[(R)-2-hydroxy-3-(2-indan-2-yl-1,1-dimethyl-ethylamino)-propoxy]-phenyl}-propionic acid;

3-{3-Bromo-4-[(R)-2-hydroxy-3-(2-indan-2-yl-1,1-dimethyl-ethylamino)-propoxy]-phenyl}-propionic acid ethyl ester;

3-{3-Bromo-4-[(R)-2-hydroxy-3-(2-indan-2-yl-1,1-dimethyl-ethylamino)-propoxy]-phenyl}-propionic acid;

3-{3-[(R)-2-Hydroxy-3-(2-indan-2-yl-1,1-dimethyl-ethylamino)-propoxy]-phenyl}-propionic acid ethyl ester;

3-{3-[(R)-2-Hydroxy-3-(2-indan-2-yl-1,1-dimethyl-ethylamino)-propoxy]-phenyl}-propionic acid; and 3-{4-[(R)-2-Hydroxy-3-(2-indan-2-yl-1,1-dimethyl-ethylamino)-propoxy]-phenyl}-propionic acid.

DETAILED DESCRIPTION OF THE INVENTION

The present application demonstrates the ability of calcilytic compounds to exert a physiologically relevant effect on a cell by illustrating the ability of such compounds to increase PTH secretion and also identifies a target site for calcilytic compounds.

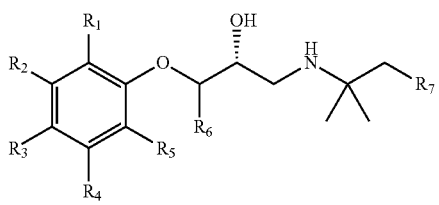

wherein:
$R_1$ and $R_5$ are independently selected from the group consisting of H and halogen
$R_2$, $R_3$ and $R_4$ are independently selected from the group consisting of H, halogen and J-K wherein:
  J is a covalent bond, alkylene or alkenyl: and K is selected from the group of $CO_2R_8$, such that $R_8$ is H or alkyl
$R_6$ is selected from the group consisting of H or alkyl
$R_7$ is selected from the group consisting of aryl or fused aryl, dihydro, tetrahydro fused aryl, heteroaryl, unsubstituted or substituted with any substituent selected from the group consisting of OH, halogen, $C_{1-4\ alkyl}$, $C_{1-4alkoxy}$, $C_{3-6\ cycloalkyl}$, $CF_3$, $OCF_3$, CN and $NO_2$,
and pharmaceutically acceptable salts and complexes thereof.
Synthesis Schemes.

The synthesis of the compounds of the general formula (I) may be prepared as outlined below in Schemes 1 and 2. Treatment of the phenol 1 with a base such as potassium carbonate in the presence of the nosyl epoxide 2 provides the epoxide intermediate 3. Treatment of 3 with an amine such as 4 in a solvent such as ethanol at elevated temperature provides the aminoalcohol 5. Heck coupling of 5 with an olefin such as ethyl acrylate provides the α,β-unsaturated ester 6 which is saponified with a base such as sodium hydroxide in ethanol and water to provide the acrylic aid derivative 7. The acrylic acid 7 is reduced under conditions which are common to the art such as hydrogen in the presence of a catalyst such as palladium on carbon to provide the acid 8 which is esterified under conditions common to the art to provide the ester 9.

As shown in Scheme 2 compounds of the general formula (I) may be prepared by halogenation of a phenol such as 3-(3-hydroxy-phenyl)-propionic acid ethyl ester 10 to provide 3-(4-bromo-3-hydroxy-phenyl)-propionic acid ethyl ester 11. The ester 11 may be converted to the epoxide 12 as described above. Epoxide 12 can be converted to the acid/ester pair 13 and 14 as described above for the synthesis of 8 and 9.

Scheme 1.

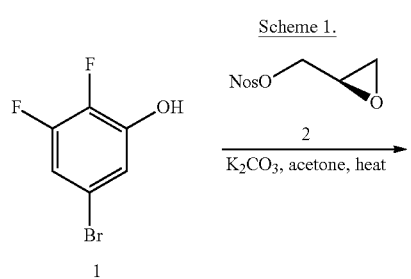

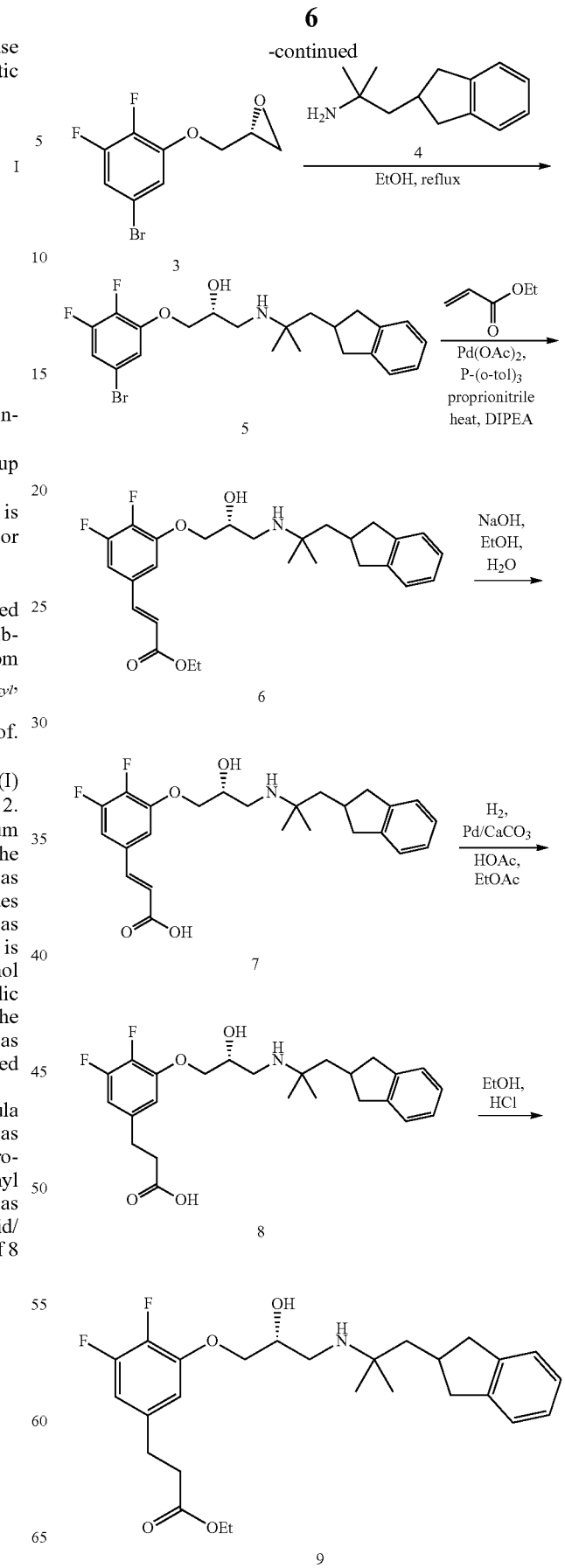

Scheme 2.

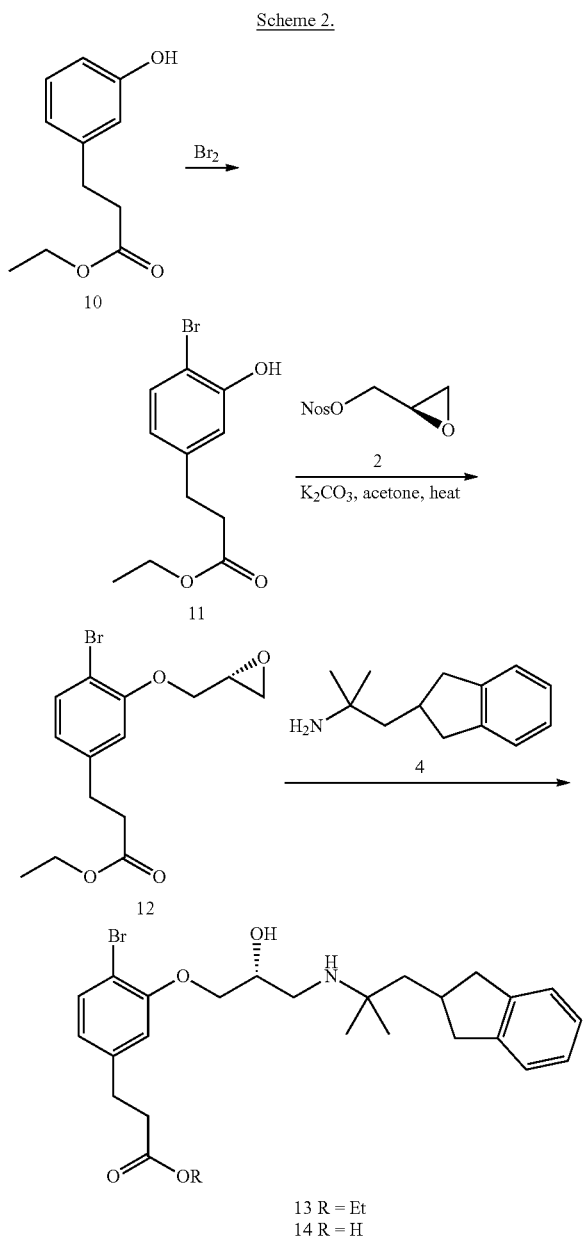

13 R = Et
14 R = H

EXPERIMENTAL PROCEDURES

The following examples are intended to be merely illustrative of the present invention and not limiting in any way.

Example 1

Preparation of (E)-3-{3,4-difluoro-5-[(R)-2-hydroxy-3-(2-indan-2-yl-1,1-dimethyl-ethylamino)-propoxy]-phenyl}-acrylic acid hydrochloride (a) (R)-2-(5-bromo-2,3-difluoro-phenoxymethyl)-oxirane To an acetone solution (0.1 M, 240 mL) of commercially available 5-bromo-2,3-difluorophenol (5.0 g, 23.93 mmol) was added $K_2CO_3$ (9.92 g, 71.77 mmol), and the mixture was heated to reflux for 30 min. After cooling this mixture to RT, (2R)-(−)-glycidyl 3-nitrobenzenesulfonate (6.20 g, 23.93 mmol) was added, and the resulting mixture was heated to reflux overnight. After cooling to RT, the solids were removed by filtration and washed well with ethyl acetate. The filtrate was concentrated and partitioned between ethyl acetate and 1N HCl. The organic portion was washed successively with 5% $NaHCO_3$ and brine, dried ($MgSO_4$), filtered and concentrated to a solid. Purification by FCC (15% ethyl acetate/hexanes) gave the product as a white solid in 97% yield (6.19 g).

(b) (R)-1-(5-bromo-2,3-difluoro-phenoxy)-3-(2-indan-2-yl-1,1-dimethyl-ethylamino)-propan-2-ol An ethanolic solution (0.2 M, 93 mL) of the oxirane of Example 1a (5 g, 18.67 mmol) and 2-indan-2-yl-1,1-dimethyl-ethylamine (free base, 3.57 g, 18.67 mmol) was heated to reflux for 12 h. After solvent removal, the crude reaction mixture was purified by FCC (5% $CH_3OH/CH_2Cl_2$) to give pure product as a yellow oil (solidifies on standing) in 84% yield (7.1 g). $^1H$ NMR (dmso-$d_6$): δ 9.05 (t, J=9.0 Hz, 1H); 8.65 (t, J=9.0 Hz, 1H); 7.40 (ddd, J=9.75, 6.4, 2.2 Hz, 1H); 7.34 (ddd, J=6.7, 2.0, 2.0 Hz, 1H); 7.18 (m, 2H); 7.10 (m, 2H); 6.0 (d, J=4.8 Hz, 1H); 4.25 (m, 1H); 4.20 (m, 2H); 3.17 (m, 1H); 3.08 (m, 2H); 2.95 (m, 1H); 2.58 (m, 3H); 1.97 (d, J=5.43 Hz, 2H); 1.39 (s, 6H). LCMS (m/z) M+H=454/456.

(c) (E)-3-{3,4-difluoro-5-[(R)-2-hydroxy-3-(2-indan-2-yl-1,1-dimethyl-ethylamino)-propoxy]-phenyl}-acrylic acid hydrochloride To a solution of the bromide of Example 1b (21.0 g, 46.26 mmol) in degassed propionitrile (0.2 M, 230 mL) were added $Pd(OAc)_2$ (0.52 g, 2.31 mmol), P(o-tol)$_3$ (2.11 g, 6.94 mmol), DIPEA (17.7 mL, 101.76 mmol), and ethyl acrylate (6.51 mL, 60.13 mmol). The reaction flask was fitted with a condenser, kept under Ar cover, and placed in a pre-heated bath (115° C.) for 3.5 h. After cooling to RT, the reaction mixture was filtered through Celite, and the filtrate was concentrated, partitioned between ethyl acetate and 1N HCl. The layers were separated and the organic portion was washed successively with 5% $NaHCO_3$ and brine, dried ($MgSO_4$), filtered and concentrated to a brown oil.

A portion of the crude residue (6.2 g) was brought up in ethanol and water (0.2 M, 50 mL, 13 mL) and treated with 2N NaOH (13 mL). The reaction mixture stirred at RT for 12 h. The ethanol was removed and the aqueous portion (pH 14) was diluted up to 200 mL and extracted 3× with 30 mL portions of diethyl ether. Aqueous HCl was added while stirring to adjust the pH to 5, causing the product come out of solution as a gum. $CH_2Cl_2$ was added, and the biphasic mixture was stirred well for 5-30 min. By this method, the product was transformed into a white solid and was isolated as pure zwitterion by filtration (3.3 g, 70% for 2 steps).

To an acetonitrile suspension of the zwitterion product was added 2M HCl in diethyl ether. The material briefly went into solution, and then precipitated as a white crystalline solid to give (E)-3-{3,4-Difluoro-5-[(R)-2-hydroxy-3-(2-indan-2-yl-1,1-dimethyl-ethylamino)-propoxy]-phenyl}-acrylic acid as the pure HCl salt. $^1H$ NMR (dmso-$d_6$): δ12.53 (s, 1H); 8.91 (m, 1H); 8.58 (m, 1H); 7.54 (d, J=16.0 Hz, 1H); 7.49 (m, 2H); 7.18 (m, 2H); 7.11 (m, 2H); 6.67 (d, J=16.0 Hz, 1H); 6.0 (d, J=4.4 Hz, 1H); 4.27 (m, 1H); 4.23 (m, 2H); 3.17 (m, 1H); 3.09 (dd, J=13.4, 7.05 Hz, 2H); 2.96 (m, 1H); 2.56 (m, 3H); 1.96 (d, J=5.4 Hz, 2H); 1.39 (s, 6H).

Example 2

Preparation of 3-{3,4-difluoro-5-[(R)-2-hydroxy-3-(2-indan-2-yl-1,1-dimethyl-ethylamino)-propoxy]-phenyl}-propionic acid hydrochloride To a solution of the acrylic acid of Example 1 (2.5 g, 5.62 mmol) in acetic acid (30 mL) and ethyl acetate (20 mL) was added 5% Pd/CaCO$_3$ (0.50 g). The reaction flask was purged with H$_2$ and sealed under a H$_2$ balloon for 15 h. The mixture was filtered through Celite, and the filtrate was concentrated to approx 5 mL volume. Toluene (100 mL) and 2M HCl in diethyl ether (10 mL) were added and the solution was concentrated to a white solid.

The solid was suspended in acetonitrile and treated with 2M HCl in diethyl ether. This solution was concentrated to dryness providing the title compound as the HCl salt as a white solid: $^1$H NMR (dmso-d$_6$): δ 9.0 (m, 1H); 8.6 (m, 1H); 7.19 (m, 2H); 7.11 (m, 2H); 6.98 (app. d, J=7.1 Hz, 1H); 6.91 (m, 1H); 6.0 (br s, 1H); 4.27 (m, 1H); 4.14 (d, J=5.1 Hz, 2H); 3.20 (m, 1H); 3.10 (m, 2H); 2.98 (m, 1H); 2.79 (t, J=7.7 Hz, 2H); 2.58 (m, 5H); 1.97 (d, J=5.4 Hz, 2H); 1.39 (s, 6H): LCMS (m/z) M+H=448.

Example 3

Preparation of 3-{3,4-difluoro-5-[(R)-2-hydroxy-3-(2-indan-2-yl-1,1-dimethyl-ethylamino)-propoxy]-phenyl}-propionic acid ethyl ester hydrochloride To a suspension of the propionic acid of Example 2 (2 g) in ethanol (20 mL) was added 2M HCl in diethyl ether (2 mL). The mixture was heated to reflux for 3 h. After cooling to RT, the resulting solution was concentrated to a yellow oil and dried under vacuum. The contents of the flask solidified to give the title compound as an HCl salt (2 g): $^1$H NMR (dmso-d$_6$): δ 9.05 (m, 1H); 8.62 (m, 1H); 7.18 (m, 2H); 7.11 (m, 2H); 6.98 (app. d, J=7.1 Hz, 1H); 6.91 (m, 1H); 6.0 (br s, 1H); 4.27 (m, 1H); 4.14 (d, J=5.2 Hz, 2H); 4.06 (q, J=7.1 Hz, 2H); 3.18 (m, 1H); 3.09 (m, 2H); 2.98 (m, 1H); 2.82 (t, J=7.5 Hz, 2H); 2.61 (m, 5H); 1.97 (d, J=5.4 Hz, 2H); 1.39 (s, 6H); 1.17 (t, J=7.1 Hz, 3H): LCMS (m/z) M+H=476.

Example 4

Preparation of 5-{3,4-difluoro-5-[(R)-2-hydroxy-3-(2-indan-2-yl-1,1-dimethyl-ethylamino)-propoxy]-phenyl}-pentanoic acid hydrochloride The title compound was prepared in two steps by the methods described above for the preparation of the compound of Example 1 except that ethyl-4-pentenoate was used instead of ethyl acrylate in the Heck coupling reaction to provide 5-{3,4-Difluoro-5-[(R)-2-hydroxy-3-(2-indan-2-yl-1,1-dimethyl-ethylamino)-propoxy]-phenyl}-pent-4-enoic acid ethyl ester. The ethyl ester product of the Heck reaction was hydrolyzed to the carboxylic acid in a manner similar to that described above. HCl salt formation was carried out by the method described above: $^1$H NMR (dmso-d$_6$): δ 8.9 (br, 1H); 8.55 (br, 1H); 7.18 (m, 2H); 7.07 (m, 5H); 6.38 (s, 1H); 5.99 (br s, 1H); 4.25 (m, 1H); 4.15 (m, 2H); 3.36 (m, 2H); 3.19 (m, 1H); 3.08 (dd, J=13.3, 7.05 Hz, 2H); 2.95 (m, 1H); 2.55 (m, 3H); 2.40 (s, 2H); 1.95 (d, J=5.3 Hz, 2H); 1.39 (s, 6H): LCMS (m/z) M+H=474.6.

Example 5

Preparation of 5-{3,4-difluoro-5-[(R)-2-hydroxy-3-(2-indan-2-yl-1,1-dimethyl-ethylamino)-propoxy]-phenyl}-pentanoic acid The title acid was prepared by hydrogenation in the presence of catalytic Pd/CaCO$_3$ in acetic acid and ethyl acetate in a manner similar to that described above in Example 2: $^1$H NMR (dmso-d$_6$): δ 8.75 (m, 1H); 8.50 (m, 1H); 7.19 (m, 2H); 7.10 (m, 2H); 6.90 (m, 2H); 5.95 (d, J=4.3 Hz, 1H); 4.22 (m, 1H); 4.15 (m, 2H); 3.4 (m, 2H); 3.20 (m, 1H); 3.10 (dd, J=13.8, 7.2 Hz, 2H); 2.98 (m, 1H); 2.60 (m, 3H); 2.24 (t, J=7.2 Hz, 2H); 1.95 (d, J=5.7 Hz, 2H); 1.56 (m, 2H); 1.51 (m, 2H), 1.38 (s, 6H): LCMS (m/z) M+H=476.

Example 6

Preparation of 5-{3,4-difluoro-5-[(R)-2-hydroxy-3-(2-indan-2-yl-1,1-dimethyl-ethylamino)-propoxy]-phenyl}-pentanoic acid ethyl ester To a solution of 5-{3,4-Difluoro-5-[(R)-2-hydroxy-3-(2-indan-2-yl-1,1-dimethyl-ethylamino)-propoxy]-phenyl}-pent-4-enoic acid ethyl ester of Example 4 (12.0 g, 23.95 mmol) in ethanol (250 mL) was added 5% Pd/CaCO$_3$ (2.4 g). The reaction flask was purged with H$_2$ and sealed under a H$_2$ balloon for 15 h. The mixture was filtered through Celite, and the filtrate was concentrated. Column chromatography of the residue (SiO$_2$, 5% CH$_3$OH/CH$_2$Cl$_2$) provided pure ester product, which was converted to the HCl salt using the method described above.

Example 7

Preparation of 3-{4-bromo-3-[(R)-2-hydroxy-3-(2-indan-2-yl-1,1-dimethyl-ethylamino)-propoxy]-phenyl}-propionic acid ethyl ester hydrochloride (a) 3-(3-hydroxy-phenyl)-propionic acid ethyl ester To a solution of commercially available 3-(3-hydroxy-phenyl)-propionic acid (25 g, 150.4 mmol) in ethanol (250 mL) was added concentrated sulfuric acid (3.0 mL). The solution was heated to reflux overnight. The solvent was removed in vacuo, and the resulting oil was diluted ethyl acetate and placed in a separatory funnel. The organic portion was extracted 2× with 5% NaHCO$_3$ and once with brine. The solution was dried (MgSO$_4$), filtered and concentrated to a dark tan oil (30 g). This material was carried on to the next step without further purification.

(b) 3-(4-bromo-3-hydroxy-phenyl)-propionic acid ethyl ester

To a −10° C. solution of 3-(3-hydroxy-phenyl)-propionic acid ethyl ester (2.0 g, 10.31 mmol) in chloroform (0.2 M, 51 mL) was added N-bromosuccinimide (1.93 g, 10.83 mmol). After stirring at RT overnight, the solution was concentrated in vacuo and purified by flash column chromatography (SiO2, 5% to 15% ethyl acetate/hexanes) to give the product as a colorless oil (0.45 g, 16%).

(c) R)-2-(5-bromo-2,3-difluoro-phenoxymethyl)-oxirane

A suspension of 3-(4-bromo-3-hydroxy-phenyl)-propionic acid ethyl ester (0.6 g, 2.20 mmol) and K$_2$CO$_3$ (0.91 g, 6.59 mmol) in acetone (0.1 M, 22 mL) was heated to reflux for 30 min. After cooling this mixture to RT, (2R)-(−)-glycidyl 3-nitrobenzenesulfonate (0.57 g, 2.20 mmol) was added, and the resulting mixture was heated to reflux overnight. The solids were removed by filtration and washed with ethyl acetate. The filtrate was concentrated and partitioned between ethyl acetate and 1N HCl. The organic portion was washed successively with 5% NaHCO$_3$ and brine, dried (MgSO$_4$), filtered and concentrated to a yellow oil.

(d) 3-{4-bromo-3-[(R)-2-hydroxy-3-(2-indan-2-yl-1,1-dimethyl-ethylamino)-propoxy]-phenyl}-propionic acid ethyl ester hydrochloride A solution of the crude oxirane (0.7 g) and 2-indan-2-yl-1,1-dimethyl-ethylamine (0.42 g, 2.2 mmol) in ethanol (0.2 M, 11 mL) was heated to reflux overnight. After solvent removal, the crude reaction mixture was purified by FCC (5% CH$_3$OH/CH$_2$Cl$_2$) to give pure product as a yellow oil. The material was dissolved in acetonitrile and CH$_2$Cl$_2$ and treated with 2M HCl in diethyl ether. Removal of the solvents and drying under vacuum provided the title compound as the HCl salt as an off-white solid (0.5 g, 44% for 2 steps). $^1$H NMR (dmso-d$_6$): δ 8.70 (m, 1H); 8.52 (m, 1H); 7.47 (d, J=8.1 Hz, 1H); 7.18 (m, 2H); 7.11 (m, 2H); 7.05 (d, J=1.7 Hz, 1H); 6.79 (dd, J=8.1, 1.6 Hz, 1H); 5.92 (d, J=4.7 Hz, 1H); 4.15 (m, 1H); 4.05 (q, J=7.1 Hz, 3H); 3.25 (m, 1H); 3.09 (m, 3H); 2.83 (t, J=7.4 Hz, 2H); 2.64 (t, J=7.4 Hz, 2H); 2.56 (m, 3H); 1.96 (d, J=5.5 Hz, 2H); 1.39 (s, 6H); 1.17 (t, J=7.1 Hz, 3H): LCMS (m/z) M+H=518/520.

Example 8

Preparation of 3-{4-bromo-3-[(R)-2-hydroxy-3-(2-indan-2-yl-1,1-dimethyl-ethylamino)-propoxy]-phenyl}-propionic acid hydrochloride To a solution of 3-{4-bromo-3-[(R)-2-hydroxy-3-(2-indan-2-yl-1,1-dimethyl-ethylamino)-propoxy]-phenyl}-propionic acid ethyl ester of Example 7 (0.25 g, 0.48 mmol) in ethanol (4 mL) and water (0.8 mL) was added 2N NaOH (0.36 mL, 0.72 mmol). The solution stirred at RT overnight. The ethanol was removed and the residue was diluted with water, adjusted to pH 6 and extracted 3× with CH$_2$Cl$_2$. The organic portion was dried (Na$_2$SO$_4$), filtered and concentrated in vacuo to give the pure zwitterion as a white solid.

To an acetonitrile suspension of the zwitterion product was added 2M HCl in diethyl ether. The material briefly went into solution, and then precipitated as a white crystalline solid to give the pure HCl salt, which was isolated by filtration and dried under vacuum (0.18 g, 76%): $^1$H NMR (dmso-d$_6$): δ 8.80 (m, 1H); 8.55 (m, 1H); 7.47 (d, J=8.1 Hz, 1H); 7.19 (m, 2H); 7.11 (m, 2H); 7.05 (d, J=1.7 Hz, 1H); 6.79 (dd, J=8.1, 1.7 Hz, 1H); 5.93 (br s, 1H); 4.25 (m, 1H); 4.16 (m, 1H); 4.05 (m, 1H); 3.26 (m, 1H); 3.09 (m, 3H); 2.80 (t, J=7.6 Hz, 2H); 2.62-2.52 (m, 5H); 1.96 (d, J=5.4 Hz, 2H); 1.39 (s, 6H): LCMS (m/z) M+H=490/492.

Example 9

Preparation of 3-{2,3-difluoro-4-[(R)-2-hydroxy-3-(2-indan-2-yl-1,1-dimethyl-ethylamino)-propoxy]-phenyl}-propionic acid hydrochloride (a) 4-bromo-2,3-difluoro-oxiranylmethoxy benzene A solution of the crude 4-bromo-2,3-difluorophenol (0.40 g) [prepared using published procedure, WO0121606] and (2R)-glycidyl 3-nitrobenzenesulfonate (0.49 g) in dry acetone (19 mL) was treated with potassium carbonate (0.79 g) and refluxed under nitrogen for 12 h. The reaction was cooled, filtered and filtrate was concentrated in vacuo and the residue was flash chomatogaphed (20% ethyl acetate/hexanes) to yield the desired product (0.33 g) in 71% yield. $^1$H-NMR (400 MHz, CDCl$_3$) δ: 7.23-7.19 (m, 1H), 6.74-6.71 (m, 1H), 4.35-4.32 (m, 1H), 4.03-3.99 (m, 1H), 3.38-3.35 (m, 1H), 2.93-2.92 (m, 1H), 2.77-2.76 (m, 1H).

(b) (R)-1-(4-bromo-2,3-difluorophenoxy)-3-(2-indan-2-yl-1,1-dimethyl-ethylamino)-propan-2-ol A mixture of 2-(5-bromo-2,3-difluorophenoxymethyl)-oxirane of Example 8a (2.12 g, 8 mmol) and 2-indan-2-yl-1,1-dimethyl-ethylamine (1.51 g, 8 mmol) were taken up in absolute ethanol (32 mL) and refluxed overnight. After all the epoxide was consumed the reaction was cooled and concentrated and flash chromatographed (10% methanol/dichloromethane) to yield the desired product (3.06 g, 84%). MS (ES) m/z 454 (M+H)$^+$.

(c) (E)-3-{2,3-difluoro-4-[(R)-2-hydroxy-3-(2-indan-2-yl-1,1-dimethyl-ethyl amino)-propoxy]-phenyl}-acrylic acid ethyl ester A 150 mL sealed tube was charged with a stirring bar, (R)-1-(4-Bromo-2,3-difluorophenoxy)-3-(2-indan-2-yl-1,1-dimethyl-ethylamino)-propan-2-ol (3.06 g) 1 and propionitrile (70 mL). To this was added Pd(OAc)$_2$ (0.151 g), P(O-tol)$_3$ (0.82 g), ethyl acrylate (1.35 g), triethylamine (2.73 g) sequentially and deoxygenated the reaction by bubbling nitrogen for 15 minutes. The sealed tube was capped tightly and immersed into a preheated (120° C.) oil bath. The reaction was heated at this temperature for 12 hrs. Cool to ambient temperature and concentrated under reduced pressure. The crude residue was purified by flash column chromatography eluting initially with 50% EtoAc in hexanes and 100% EtOAc. At this time the eluting solvent mixtures were switched to 100% dichloromethane, 5% MeOH in dichloromethane followed by 8% MeOH in dichloromethane. The product was collected and concentrated to get the desired product (2.40 g, 75%) as pale yellow foam. MS (ES) m/z 474 [M+H]$^+$.

(d) 3-{2,3-difluoro-4-[(R)-2-hydroxy-3-(2-indan-2-yl-1,1-dimethyl-ethyl amino)-propoxy]-phenyl}-propionic acid ethyl ester The 250 mL round bottom flask was equipped with a magnetic stir bar, the compound of Example 8 (2.40 g), 100 mL of absolute ethanol. To this was added 0.24 grams (10% w/w) of catalyst (Pd/CaCO$_3$) and placed under hydrogen atmosphere. After 16 h of stirring all starting material was consumed. The reaction mixture was filtered through a pad of celite and washed with additional amount of ethanol and concentrated to provide the crude product (2.35 g, 98%). MS (ES) m/z 476 [M+H]$^+$.

(e) 3-{2,3-difluoro-4-[(R)-2-hydroxy-3-(2-indan-2-yl-1,1-dimethyl-ethyl amino)-propoxy]-phenyl}-propionic acid hydrochloride A solution of the ester (1.6 g) in ethanol (30 mL) was treated with 2.5 N NaOH (6 mL) and stirred at RT under argon overnight. The ethanol was removed in vacuo and the aqueous layer was diluted with water (10 mL) and then extracted with ether (3×20 mL). The aqueous layer was collected and the pH was adjusted to pH 5 with conc. HCl while stirring. The precipitated white solid was collected by filtration and air dried to afford 1.3 g (86%) of a white solid: MS (ES) m/z 448 [M+H]+.

This acid (0.65 g) was suspended in dry acetonitrile (15 mL) and treated with 2.0M HCl (4 mL) in ether. The reaction mixture became homogeneous after few minutes then a white solid crashed out. The reaction was stirred for additional 10 minutes upon which it was filtered and dried to provide the title compound (0.52 g, 74%). MS (ES) m/z 448 [M+H]+. $^1$H NMR (400 MHz, DMSO-$d_6$): 8.63 (s, 1H), 8.39 (s, 1H), 7.13-6.90 (m, 6H), 5.86 (d, 1H), 4.14 (brs, 1H), 4.05 (d, 2H), 3.13-3.09 (m, 1H), 3.04 and 3.00 (dd, 2H), 2.93-2.89 (m, 1H), 2.75 (t, 2H), 2.55-2.44 (m, 5H), 1.89 (d, 2H), 1.31 (s, 6H).

Example 10

Preparation of 3-{2,3-difluoro-4-[(R)-2-hydroxy-3-(2-indan-2-yl-1,1-dimethyl-ethyl amino)-propoxy]-phenyl}-propionic acid hydrochloride The acid of Example 9 (0.65 g) was dissolved in absolute ethanol (10 mL) and catalytic amount of conc. sulfuric acid was added. The reaction was stirred and heated to reflux overnight. The reaction was concentrated, then diluted with ethyl acetate and washed with 2.5N NaOH (2×10 mL), brine (10 mL), dried over sodium sulfate. The filtrate was concentrated and purified by HPLC and converted to the HCl salt utilizing the standard protocol. MS (ES) m/z 476 [M+H]+. $^1$H NMR (400 MHz, DMSO-$d_6$): 68.72 (s, 1H), 8.48 (s, 1H), 7.20-6.99 (m, 6H), 5.93 (d, 1H), 4.20 (brs, 1H), 4.12 (d, 2H), 4.04 (q, 2H), 3.20-3.16 (m, 1H), 3.11 and 3.07 (dd, 2H), 3.00-2.96 (m, 1H), 2.85 (t, 2H), 2.62-2.51 (m, 5H), 1.95 (d, 2H), 1.37 (s, 6H), 1.15 (t, 3H).

Example 11

Preparation of (E)-3-{2,3-dichloro-5-[(R)-2-hydroxy-3-(2-indan-2-yl-1,1-dimethyl-ethylamino)-propoxy]-phenyl}-acrylic acid hydrochloride (a) 4-bromo-2,3-dichlorophenol In a 250 mL round bottom flask 10 g of 2,3-dichlorophenol was dissolved in a solvent mixture of glacial acetic acid (16 mL) and chloroform (4 mL) and cooled to 10° C. To this was added bromine (3.45 mL) in 15 mL of glacial acetic acid dropwise while maintaining the temperature. The reaction was vigorously stirred while adding bromine and continued stirring vigorously 0.5 h after addition was finished. At this time reaction mixture was poured into a flask containing 60 mL of water and 30 mL of dichloromethane. Organic layer was separated and aqueous layer was extracted with dichloromethane (3×50 mL). The organic layers were combined and washed with Sat. sodium bicarbonate (3×100 mL) and brine (100 mL) and dried over sodium sulfate. The crude product (9.65 g) was carried in to the next step without any purification. $^1$H-NMR (400 MHz, CDCl$_3$) δ: 7.47 and 6.89 (ABq, 2H), 5.69 (brs, 1H).

(b) 4-bromo-2,3-dichloro-oxiranylmethoxy benzene

A solution of the crude 4-bromo-2,3-dichlorophenol (7.96 g) and (2R)-glycidyl 3-nitrobenzenesulfonate (8.52 g) in dry acetone (250 mL) was treated with potassium carbonate (13.61 g) and refluxed under nitrogen for 12 h. The reaction was cooled, filtered and filtrate was concentrated in vacuo and the residue was flash chromatographed (20% ethyl acetate/hexanes) to yield the desired product (6.94 g) in 71% yield. $^1$H-NMR (400 MHz, CDCl$_3$) δ: 7.48 and 6.82 (d, 2H), 4.37 and 4.34 (dd, 1H), 4.06 and 4.03 (dd, 1H), 3.42-3.39 (m, 1H), 2.96-2.94 (m, 1H), 2.85-2.83 (m, 1H).

(c) (R)-1-(4-bromo-2,3-dichloro-phenoxy)-3-(2-indan-2-yl-1,1-dimethyl-ethylamino)-propan-2-ol A mixture of the epoxide (0.5 g) and indanyl amine (0.32 g) were taken up in absolute ethanol (16 mL) and refluxed overnight. After all the epoxide was consumed the reaction was cooled and concentrated and purified by flash chromatography (10% methanol/dichloromethane) to yield 86% of the desired product (0.71 g). MS (ES) m/e 488 [M+H]+.

(d) (E)-3-{2,3-dichloro-4-[(R)-2-hydroxy-3-(2-indan-2-yl-1,1-dimethyl-ethyl amino)-propoxy]-phenyl}-acrylic acid ethyl ester A 75 mL sealed tube was charged with a stir bar, the bromide (0.9 g) and propionitrile (10 mL). To this was added Pd(OAc)$_2$ (0.042 g) and P(O-tol)$_3$ (0.23 g), ethyl acrylate (0.40 mL) sequentially and deoxygenated the reaction by bubbling nitrogen for 15 minutes. The sealed tube was capped tightly and immersed into a preheated (120° C.) oilbath. The reaction was heated at this temperature for 12 h. Cool to ambient temperature and concentrated under reduced pressure. The crude residue was purified by flash column chromatography eluting initially with 50% EtoAc in hexanes and 100% EtoAc. At this time the eluting solvent mixtures were switched to 100% DCM, 5% MeOH in dichloromethane followed by 8% MeOH in DCM. The product was collected and concentrated to get the desired product (0.95 g) in 98% yield as pale yellow foam. MS (ES) m/e 506 [M+H]+.

(e) (E)-3-{2,3-dichloro-4-[(R)-2-hydroxy-3-(2-indan-2-yl-1,1-dimethyl-ethyl amino)-propoxy]-phenyl}-acrylic acid hyrdrochloride A solution of the ester (5.0 g) in ethanol (49 mL) was treated with 2.5 N NaOH (4.5 mL) and stirred under argon overnight. The ethanol was removed in vacuo and the aqueous layer was diluted with water (10 mL) and then extracted with ether (3×100 mL). The aqueous layer was collected and the pH was adjusted to pH 4 with conc. HCl while stirring. The precipitated white solid was collected by filtration and air dried to afford the title compound (3.92 g, 83%). MS (ES) m/e 478 [M+H]+. $^1$H-NMR (400 MHz, DMSO-$d_6$) δ: 7.76 and 7.15 (ABQ, 2H), 7.66 (d, 1H), 7.06-6.97 (m, 4H), 6.41 (d, 1H), 4.12-3.92 (m, 3H), 3.20 (brs, 1H), 2.95 and 2.92 (dd, 2H), 2.84 and 2.81 (dd, 2H), 2.70 and 2.67 (dd, 2H), 2.50-2.43 (m, 2H), 1.67 (d, 2H), 1.10 (s, 6H).

Example 12

Preparation of 3-{2,3-chloro-4-[(R)-2-hydroxy-3-indan-2-dimethyl-ethylamino)-propoxy]-phenyl}-propionic acid hydrochloride A 250 mL round bottom flask was equipped with a magnetic stir bar, the acrylic acid of Example 11 (2.0 g), 100 mL of absolute ethanol and 50 mL of methanol. To this was added 0.2 g (10% w/w) of catalyst (5% Rhodium/Al$_2$O$_3$) and placed under hydrogen atmosphere. After 16 h of stirring all starting material was consumed. The reaction mixture was filtered though a pad of celite and washed with additional amount of methanol and concentrated to get the desired product (1.96 g) in 98% yield. MS (ES) m/e 480.2 [M+H]$^+$.

The acid (0.5 g) was suspended in dry acetonitrile (10 mL) and treated with 1.0M HCl (5.2 mL) in ether. The reaction stirred for 15 minutes then concentrated to give pale yellow foam in quantitative yield. MS (ES) m/e 480.2 [M+H]$^+$. $^1$H-NMR (400 MHz, DMSO-d$_6$) δ:8.64 (t, 1H), 8.45 (t, 1H), 7.27 (d, 1H), 7.15-7.04 (m, 4H), 5.86 (d, 1H), 4.20-4.03 (m, 3H), 3.37-2.82 (m, 10H), 2.55-2.45 (m, 2H), 1.93 (d, 2H), 1.35 (s, 6H).

Example 13

Preparation of 3-{2,3-chloro-4-[(R)-2-hydroxy-3-(2-indan-2-yl-1,1-dimethyl-ethylamino)-propoxy]-phenyl}-propionic acid ethyl ester trifluoroacetate The acid of Example 12 (2.0 g) was dissolved in absolute ethanol (50 mL) and catalytic amount of conc. sulfuric acid was added. The reaction was stirred and heated to reflux overnight. Next day the reaction was concentrated and diluted with ethyl acetate and washed with 2.5N NaOH (2×20 mL), brine (20 mL) and dried over sodium sulfate. MS (ES) m/e 508 [M+H]$^+$.

The ethyl ester (33.7 g) was dissolved in dry acetonitrile and placed under inert atmosphere. To this was added 6 mL of trifluoroacetic acid stirred for 15 minutes and concentrated to give thick pale yellow syrup in quantitative yield (41.2 g). MS (ES) m/e 508 [M+H]$^+$. $^1$H-NMR (400 MHz, DMSO-d$_6$) δ: 8.35 (brs, 2H), 7.31 (d, 1H), 7.20-7.08 (m, 5H), 5.91 (brs, 1H), 4.20-4.02 (m, 5H), 3.27-3.20 (m, 1H), 3.09, 3.05 (dd, 1H), 2.95 (t, 1H), 2.61-2.47 (m, 5H), 1.93 (d, 2H), 1.35 (s, 6H), 1.28 (d, 3H), 1.16 (t, 3H).

Example 14

Preparation of 3-{4-fluoro-3-[(R)-2-hydroxy-3-(2-indan-2-yl-1,1-dimethyl-ethylamino)-propoxy]-phenyl}-propionic acid ethyl ester hydrochloride (a) (R)-2-(5-bromo-2-fluoro-phenoxymethyl)-oxirane A solution of the crude 5-bromo-2-fluorophenol (4.0 g) prepared using literature procedure [EP0238272] and (2R)-glycidyl 3-nitrobenzenesulfonate (5.37 g) in dry acetone (175 mL) was treated with potassium carbonate (8.58 g) and refluxed under nitrogen for 12 h. The reaction was cooled, filtered and filtrate was concentrated in vacuo and the residue was flash chromatographed (20% ethyl acetate/hexanes) to yield the desired product (4.25 g) in 82% yield. $^1$H NMR (400 MHz, CDCl$_3$): δ7.15-6.96 (m, 3H), 4.33 and 4.30 (dd, 1H), 4.02 and 4.00 (dd, 1H), 3.41-3.37 (m, 1H), 2.97 (m, 1H), 2.78 (m, 1H).

(b) (R)-1-(5-bromo-2fluoro-phenoxy)-3-(2-indan-2-yl-1,1-dimethyl-ethylamino)-propan-2-ol A mixture of the epoxide (3.0 g) and indanyl amine (2.24 g) were taken up in absolute ethanol (60 mL) and refluxed overnight. After all the epoxide was consumed the reaction was cooled and concentrated and purified by flash chromatography (10% methanol/dichloromethane) to yield 87% of the desired product (4.55 g). MS (ES) m/e 437 [M+H]$^+$.

(c) (E)-3-{4-fluoro-3-[(R)-2-hydroxy-3-(2-indan-2-yl-1,1-dimethyl-ethyl amino)-propoxy]-phenyl}-acrylic acid ethyl ester A sealed tube was charged with a stir bar, the bromide (5.20 g) and propionitrile (60 mL). To this was added Pd(OAc)$_2$ (0.54 g) and P(O-tol)$_3$ (2.91 g), ethyl acrylate (1.95 mL) sequentially and deoxygenated the reaction by bubbling nitrogen for 15 minutes. The sealed tube was capped tightly and immersed into a preheated (120° C.) oil bath. The reaction was heated at this temperature for 12 h. Cool to ambient temperature and concentrated under reduced pressure. The crude residue was purified by flash column chromatography eluting initially with 50% EtOAc in hexanes and 100% EtOAc. At this time the eluting solvent mixtures were switched to 100% DCM, 5% MeOH in dichloromethane followed by 8% MeOH in DCM. The product was collected and concentrated to get the desired product (4.81 g) in 88% yield as pale yellow foam. MS (ES) m/e 556 [M+H]$^+$.

(d) 3-{4-fluoro-3-[(R)-2-hydroxy-3-(2-indan-2-yl-1, 1-dimethyl-ethyl amino)-propoxy]-phenyl pent-4-enoic acid ethyl ester hydrochloride The 250 ml round bottom flask was equipped with a magnetic stir bar, ethyl acrylate (3.2 g, 7 mmol), 100 ml of absolute ethanol. To this was added 0.32 grams (10% w/w) of catalyst (Pd/CaCO$_3$) and placed under hydrogen atmosphere. After 16 h of stirring all starting material was consumed. The reaction mixture was filtered through a pad of celite and washed with additional amount of ethanol and concentrated to get the desired product 7 (3.12 g, 97%). MS (ES) m/z 458 [M+H]$^+$.

The ester 7 (0.5 g, 1 mmol) was suspended in dry acetonitrile (10 mL) and treated with 2.0M HCl (3 mL, 5 equiv.) in ether. The reaction mixture became homogeneous after few minutes then white solid crashed out. Reaction was stirred for additional 10 minutes upon which it was filtered and dried to get the desired salt (0.43 g, 80%). MS (ES) m/z 458 [M+H]$^+$. $^1$H NMR (400 MHz, DMSO-d$_6$): δ 8.56 (s, 1H), 8.45 (s, 1H), 7.28-7.15 (m, 6H) 6.91-6.88 (m, 1H), 5.98 (d, 1H), 4.26 (brs, 1H), 4.19-4.14 (m, 2H), 4.13 (q, 2H), 3.30-3.24 (m, 1H), 3.18 and 3.14 (dd, 2H), 3.09-3.02 (m, 1H), 2.90 (t, 2H), 2.71-2.57 (m, 5H), 2.02 (d, 2H), 1.45 (s, 6H), 1.28 (t, 3H).

Example 15

Preparation of 3-{4-fluoro-3-[(R)-2-hydroxy-3-(2-indan-2-yl-1,1-dimethyl-ethylamino)-propoxy]-phenyl}-propionic acid hydrochloride A solution of ester of Example 14 (2.58 g, 5.6 mmol) in ethanol (250 ml) was treated with 2.5 N NaOH (10 mL, 4.5 eq.) and stirred at room temperature under argon overnight. The ethanol was removed in vacuo and the aqueous layer was diluted with water (30 ml) and then extracted with ether (3×100 ml). The aqueous layer was collected and the pH was adjusted to pH 5 with conc. HCl while stirring. The precipitated white solid was collected by filtration and air dried to afford the title compound 8 (1.98 g, 81%). MS (ES) m/z 430 [M+H]$^+$ The acid 8 (0.10 g, 0.23 mmol) was suspended in dry acetonitrile (5 mL) and treated with 2.0M HCl (1 mL, 5 equiv.) in ether. The reaction mixture became homogeneous after few minutes then white solid crashed out. Reaction was stirred for additional 10 minutes upon which it was filtered and dried to get the desired salt (96 mg, 89%). MS (ES) m/z 430 [M+H]⁺. ¹H NMR (400 MHz, DMSO-d₆): δ8.61 (t, 1H), 8.43 (t, 1H), 7.20-7.07 (m, 6H), 6.84-6.81 (m, 1H), 5.91 (s, 1H), 4.20 (brs, 1H), 4.12-4.07 (m, 2H), 3.22-3.17 (m, 1H), 3.11 and 3.07 (dd, 2H), 3.01-2.97 (m, 1H), 2.79 (t, 2H), 2.62-2.49 (m, 5H), 1.95d, 2H), 1.38 (s, 6H).

Example 16

Preparation of 3-{2-chloro-5-[(R)-2-hydroxy-3-(2-indan-2-yl-1,1-dimethyl-ethylamino)-propoxy]-phenyl}-propionic acid ethyl ester hydrochloride (a) 3-(2-chloro-5-hydroxy-phenyl)-propionic acid ethyl ester To a 0° C. solution of 3-(3-hydroxy-phenyl)-propionic acid ethyl ester (1.0 g, 5.15 mmol) in diethyl ether (50 ml) was added sulfuryl chloride (0.493 mL, 6.18 mmol). After 2.5 h at 0° C., the reaction was quenched with sat. sodium carbonate (50 ml). The aqueous layer was extracted with ethyl acetate. The organic portions were combined and dried with magnesium sulfate. The solvent was removed in vacuo to afford crude product, which was purified by column chromatography (10% ethyl acetate/hexanes). The title compound was obtained as colorless oil (0.73 g, yield 62%): ¹H NMR (CDCl₃) δ 6.96 (d, J=10.1 Hz, 1H); 6.54 (d, J=2.97 Hz, 1H); 6.46 (dd, J=8.6, 3.0 Hz, 1H); 3.96 (dd, J=12.5 5.3 Hz, 2H); 2.82-2.78 (m, 2H); 1.08-1.00 (m, 3H).

(b) 3-{2-chloro-5-[(R)-2-hydroxy-3-(2-indan-2-yl-1,1-dimethyl-ethylamino)-propoxy]-phenyl}-propionic acid ethyl ester hydrochloride Utilizing the procedures described above in Examples 1a-b 3-(2-chloro-5-hydroxy-phenyl)-propionic acid ethyl ester was converted to the title compound LCMS (m/z) M+H=474.4

Example 17

Preparation of 3-{2-chloro-5-[(R)-2-hydroxy-3-(2-indan-2-yl-1,1-dimethyl-ethylamino)-propoxy]-phenyl}-propionic acid hydrochloride The ethyl ester of Example 16 was saponified to provide the title compound: ¹H NMR (DMSO) δ 8.78 (s, 1H); 8.46 (s, 1H); 7.36 (d, J=8.7 Hz, 2H); 7.20-7.18 (m, 2H); 7.12-716 (m, 2H); 6.90 (s, 1H); 6.86 (d, J=3.0 Hz, 1H); 4.02-3.98 (m, 2H); 3.36-3.32 (m, 2H); 3.12-3.04 (m, 2H); 2.90-2.84 (m, 2H); 2.62-2.44 (m, 6H); 1.38 (s, 6H): LCMS (m/z) M+H=446/448.

Example 18

Preparation of 3-{2,4-dichloro-5-[(R)-2-hydroxy-3-(2-indan-2-yl-1,1-dimethyl-ethylamino)-propoxy]-phenyl}-propionic acid ethyl ester To a solution of 3-{3-[(R)-2-hydroxy-3-(2-indan-2-yl-1,1-dimethyl-ethylamino)-propoxy]-phenyl}-propionic acid ethyl ester (0.35 g, 0.683 mmol, obtained from 3-(3-hydroxy-phenyl)-propionic acid ethyl ester by methods described herein) in chloroform (6.8 mL) was added N-chlorosuccinimide (0.27 g, 2.05 mmol) at RT. The reaction was heated to reflux overnight. Solvent was removed in vacuo, and the crude product was purified by reverse phase HPLC (65% CH₃CN/H₂O with 0.1% TFA). Pure product was obtained as white solid (0.12 g, yield 30%): ¹H NMR (CDCl₃) δ 7.2 (s, 1H); 7.26 (s, 1H); 7.18-7.12 (m, 4H); 6.86 (s, 1H); 4.51 (s, 1H); 4.28-4.18 (m, 2H); 4.16-4.12 (m, 2H); 3.40 (m, 1H); 3.22-3.18 (m, 2H); 3.14 (dd, J=15, 7.6 Hz, 2H); 3.00 (t, J=7.5 Hz, 2H); 2.26-2.22 (m, 2H); 2.60 (t, J=7.5 Hz, 2H); 2.54 (m, 1H); 2.08 (m, 2H); 1.52 (s, 6H); 1.26 (t, J=7.1 Hz, 3H): LCMS (m/z) M+H=508/510/512.

Example 19

Preparation of 5-{2,3-dichloro-4-[(R)-2-hydroxy-3-(2-indan-2-yl-1,1-dimethyl-ethylamino)-propoxy]-phenyl}-pentanoic acid (a) (E)-3-{2,3-dichloro-4-[(R)-2-hydroxy-3-(2-indan-2-yl-1,1-dimethyl-ethylamino)-propoxy]-phenyl}-pent-4-enoic acid ethyl ester A 75 mL sealed tube was charged with a stir bar, (R)-1-(4-bromo-2,3-dichloro-phenoxy)-3-(2-indan-2-yl-1,1-dimethyl-ethylamino)-propan-2-ol of Example 11c (2.0 g) and propionitrile (50 mL). To this was added Pd(OAc)₂ (0.09 g) and P(O-tol)₃ (0.5 g), ethyl 4-pentenoate (1.05 g) and diisopropylethylamine (2.08 mL) sequentially and deoxygenated the reaction by bubbling nitrogen for 15 minutes. The sealed tube was capped tightly and immersed into a preheated (120° C.) oilbath. The reaction was heated at this temperature for 12 h. Cool to ambient temperature and concentrated under reduced pressure. The crude residue was purified by flash column chromatography eluting initially with 50% EtoAc in hexanes and 100% EtoAc. At this time the eluting solvent mixtures were switched to 100% dichloromethane, 5% MeOH in dichloromethane followed by 8% MeOH in dichloromethane. The product was collected and concentrated to provide the title compound (2.0 g) in 92% yield as pale yellow foam. MS (ES) m/e 534 [M+H]⁺.

(b) (E)-3-{2,3-dichloro-4-[(R)-2-hydroxy-3-(2-indan-2-yl-1,1-dimethyl-ethyl amino)-propoxy]-phenyl}-pent-4-enoic acid A solution of ester of Example 19a (2.0 g) in ethanol (25 mL) as treated with 2.5 N NaOH (6 mL) and stirred under nitrogen overnight. The ethanol was evoporated and the aqueous layer was diluted with water (10 mL) and then extracted with ether (3×100 mL). The pH of the aqueous layer was adjusted to pH 5 with concentrated HCl and extracted with dichloromethane, dried and concentrated to give pale yellow foam in 81% yield (1.53 g). MS (ES) m/e 506 [M+H]⁺.

(c) 3-{2,3-dichloro-4-[(R)-2-hydroxy-3-(2-indan-2-yl-1,1-dimethyl-ethyl amino)-propoxy]-phenyl pent-4-enoic acid trifluoroacetate A 250 mL round bottom flask was equipped with a magnetic stir bar, the acid of Example 19b (1.0 g), 100 mL of absolute ethanol and 50 mL of methanol. To this was added 0.2 g (10% w/w) of catalyst (5% Rhodium/Al₂O₃) and placed under hydrogen atmosphere. After 16 h of stirring all starting material was consumed. The reaction mixture was filtered though a pad of Celite and washed with additional amount of methanol and concentrated. The resulted pale yellow syrup was purified by HPLC (eluted with CH₃CN/H₂O containing 0.1% TFA) to produce the desired product in 72% yield (0.88 g). MS (ES) m/e 508 [M+H]⁺. ¹H-NMR (400 MHz, DMSO-d₆) δ: 8.19 (brs, 2H), 7.14 (d, 1H), 7.03-6.92 (m, 5H), 5.77 (brs, 1H), 4.05-3.91 (m, 2H), 3.13-3.05 (m, 2H), 2.97-2.88

(m, 4H), 2.55-2.35 (m, 4H), 2.08 (t, 2H), 1.77 (d, 2H), 1.63-1.58 (m, 2H), 1.37-1.35 (m, 2H), 1.20 (d, 6H).

Example 20

Preparation of 3-{2,3-dichloro-4-[(R)-2-hydroxy-3-(2-indan-2-yl-1,1-dimethyl-ethyl amino)-propoxy]-phenyl pent-4-enoic acid ethyl ester trifluoroacetate The acid of Example 19 (0.5 g) was dissolved in absolute ethanol (10 mL) and catalytic amount of conc. sulfuric acid was added. The reaction was stirred and heated to reflux overnight. Next day the reaction was concentrated and diluted with ethyl acetate and washed with 2.5N NaOH (2×20 mL), brine (20 mL) and dried over sodium sulfate. The crude mixture was purified by HPLC (eluted with $CH_3CN/H_2O$ containing 0.1% TFA) to produce the desired product in 81% yield (0.43 g). MS (ES) m/e 536 [M+H]$^+$. $^1$H-NMR (400 MHz, DMSO-$d_6$) δ:8.35-8.48 (brs, 2H), 7.31-7.10 (m, 6H), 4.17-4.01 (m, 5H), 3.26-3.05 (m, 4H), 2.69-2.50 (m, 7H), 2.32 (t, 2H), 1.94 (d, 2H), 1.58-1.54 (t, 2H), 1.33 (s, 3H), 1.35 (s, 3H), 1.18 (t, 3H).

Example 21

Preparation of 3-{2,3-dichloro-4-[2-(R)-hydroxy-3-(2-indan-2-yl-1,1-dimethyl-ethyl amino)-1(R)-methyl-propoxy]-phenyl propionic acid ethyl ester hydrochloride 3-{2,3-dichloro-4-[2-(S)-hydroxy-3-(2-indan-2-yl-1,1-dimethyl-ethyl amino)-1(S)-methyl-propoxy]-phenyl propionic acid ethyl ester hydrochloride 3-{2,3-dichloro-4-[2(-R)-hydroxy-3-(2-indan-2-yl-1,1-dimethyl-ethyl amino)-1(S)-methyl-propoxy]-phenyl propionic acid ethyl ester hydrochloride 3-{2,3-dichloro-4-[2-(S)-hydroxy-3-(2-indan-2-yl-1,1-dimethyl-ethyl amino)-1(R)-methyl-propoxy]-phenyl propionic acid ethyl ester hydrochloride (a) 1-bromo-2,3-dichloro-4-(1-methyl-allyloxy)-benzene To a cold mixture of but-3-ene-1-ol (1.29 g) 4-bromo-2,3-dichlorophenol (4.35 g) was added triphenylphosphine (5.65 g) and DEAD (3.69 g) sequentially. Reaction was slowly warmed to room temperature while stirring. After 12 h the reaction was concentrated and the crude residue was purified by flash column chromatography eluting with EtOAc in hexanes to get the desired product (3.83 g) in 72% yield as pale yellow foam. $^1$H-NMR (400 MHz, CDCl$_3$) δ: 7.44 and 6.77 (ABq, 2H), 5.95-5.87 (m, 1H), 5.31-5.20 (m, 2H), 4.81-4.78 (m, 1H), 1.52 (d, 3H).

(b) 2-[1-(4-bromo-2,3-dichloro-phenoxy)-ethyl]-oxirane

1-Bromo-2,3-dichloro-4-(1-methyl-allyloxy)-benzene (2.5 g), 1,1,1-trifluoroacetone (6.05 mL) and sodium bicarbonate (2.12 g) were taken up in a solvent mixture of acetonitrile and water (2:1, 45 mL) and cooled to 0° C. Oxone (5.19 g) was added in three portions and the reaction was slowly warmed to room temperature. Upon completion the reaction was filtered and concentrated and re-dissolved in ethyl acetate. This solution was washed with saturated NH$_4$Cl, brine and dried over sodium sulfate. Upon filtration, it was concentrated and purified by flash column chromatography eluting with EtOAc in hexanes to get the desired product (2.39 g) in 91% yield as white solid. $^1$H-NMR (400 MHz, CDCl$_3$) δ: 7.48 (d, 2H), 6.97 (d, 1H), 6.83 (d, 1H), 4.40-4.38 (m, 1H), 4.15-4.08 (m, 1H), 3.25-3.21 (m, 1H), 3.18-3.16 (m, 1H), 2.89 (t, 1H), 2.85-2.68 (m, 3H), 1.49-1.44 (m, 6H).

(c) 3-(4-bromo-2,3-dichloro-phenoxy)-1-(2-indan-2-yl-1,1-dimethyl-ethylamino)-butan-2-ol A mixture of the epoxide (4.44 g) and indanyl amine (2.69 g) were taken up in absolute ethanol (16 mL) and refluxed overnight. After all the epoxide was consumed the reaction was cooled, concentrated and flash chromatographed (10% methanol/dichloromethane) to yield 93% of the desired product (6.61 g). MS (ES) m/e 502.4 [M+H]$^+$.

(d) (E)-3-{2,3-dichloro-4-[2-hydroxy-3-(2-indan-2-yl-1,1-dimethyl-ethyl amino)-1-methyl-propoxy]-phenyl}-acrylic acid ethyl ester A 75 mL sealed tube was charged with a stir bar, the bromide of Example 21c (5.0 g) and propionitrile (100 mL) this was added Pd(OAc)$_2$ (0.22 g) and P(O-tol)$_3$ (1.22 g) ethyl acrylate (2.17 mL) and N,N-diisopropylethylamine (7.10 mL) sequentially and deoxygenated the reaction by bubbling nitrogen for 15 minutes. The sealed tube was capped tightly and immersed into a preheated (120° C.) oil bath. The reaction was heated at this temperature for 12 h. Cool to ambient temperature and concentrated under reduced pressure. The crude residue was purified by flash column chromatography eluting initially with 50% EtOAc in hexanes and 100% EtOAc. At this time the eluting solvent mixtures were switched to 100% dichloromethane, 5% MeOH in dichloromethane followed by 8% MeOH in dichloromethane. The product was collected and concentrated to provide the desired product (5.10 g) in 98% yield as pale yellow foam. MS (ES) m/e 520 [M+H]$^+$.

(e) (E)-3-{2,3-dichloro-4-[2-hydroxy-3-(2-indan-2-yl-1,1-dimethyl-ethyl amino)-1-methyl-propoxy]-phenyl}-propoxy]-phenyl}-acrylic acid A solution of ester of Example 21d (5.0 g) in ethanol (100 mL) was treated with 2.5 N NaOH (16 mL) and stirred at room temperature under argon overnight. The ethanol was removed under pressure and the aqueous layer was diluted with water (10 mL) and then extracted with ether (3×100 mL). The aqueous layer was collected and the pH was adjusted to 4 with conc. HCl. The precipitated white solid was collected by filtration and air dried to afford the diastereomeric mixtures in 77% yield (3.64 g). MS (ES) m/e 492 [M+H]$^+$.

(f) 3-{2,3-dichloro-4-[2-hydroxy-3-(2-indan-2-yl-1,1-dimethyl-ethyl amino)-1-methyl-propoxy]-phenyl propionic acid The 250 mL round bottom flask was equipped with a magnetic stir bar, the acrylic acid of Example 21e (0.58 g) 20 mL of absolute ethanol. To this was added 0.2 g (10% w/w) of catalyst (5% Rhodium/Al$_2$O$_3$) and placed under hydrogen atmosphere. After 48 h of stirring all starting material was consumed. The reaction mixture was filtered though a pad of celite and washed with additional amount of methanol and concentrated to get the desired product as a mixture of diastereomers (0.58 g). MS (ES) m/e 494 [M+H]+.

(g) 3-{2,3-dichloro-4-[2-(R)-hydroxy-3-(2-indan-2-yl-1,1-dimethyl-ethyl amino)-1(R)-methyl-propoxy]-phenyl propionic acid ethyl ester hydrochloride 3-{2,3-Dichloro-4-[2-(S)-hydroxy-3-(2-indan-2-yl-1,1-dimethyl-ethyl amino)-1(S)-methyl-propoxy]-phenyl propionic acid ethyl ester hydrochloride 3-{2,3-Dichloro-4-[2(-R)-hydroxy-3-(2-indan-2-yl-1,1-dimethyl-ethyl amino)-1(S)-methyl-propoxy]-phenyl propionic acid ethyl ester hydrochloride 3-{2,3-Dichloro-4-[2-(S)-hydroxy-3-(2-indan-2-yl-1,1-dimethyl-ethyl amino)-1(R)-methyl-propoxy]-phenyl propionic acid ethyl ester hydrochloride The acid of Example 20f (2.50 g) was dissolved in absolute ethanol and catalytic amount of conc. sulfuric acid was added. The reaction was stirred and heated to reflux overnight. The next day the reaction was concentrated and diluted with ethyl acetate and washed with 2.5N NaOH, brine and dried ($Na_2SO_4$). The crude residue was purified by flash column chromatography eluting initially with 50% EtOAc in hexanes and 100% EtOAc. At this time the eluting solvent mixtures were switched to 100% dichloromethane, 5% MeOH in dichloromethane followed by 8% MeOH in DCM. The product was collected and concentrated to get the desired product (0.8 g) of pure product(s) and another 0.7 grams with 10% impurity. The pure product containing all four diastereoisomers was seperated by HPLC to give 100-250 mgs of each individual diastereoisomer in greater than 99% purity. MS (ES) m/e 522 [M+H]+.

Each pure stereoisomer was suspended in dry acetonitrile and treated with 1.0M HCl in ether. After 15 minutes reaction was concentrated to provide the title compounds as pure disteromers: Each individual diastereomer possessed a molecular weight by mass spectral analysis which was consistent with the molecular formula MS (ES) m/e 522 [M+H]+.

Example 22

Preparation of 3-{2,3-dichloro-4-[2-(R)-hydroxy-3-(2-indan-2-yl-1,1-dimethyl-ethyl amino)-1(R)-methyl-propoxy]-phenyl propionic acid hydrochloride 3-{2,3-dichloro-4-[2-(S)-hydroxy-3-(2-indan-2-yl-1,1-dimethyl-ethyl amino)-1(S)-methyl-propoxy]-phenyl propionic acid hydrochloride 3-{2,3-dichloro-4-[2(-R)-hydroxy-3-(2-indan-2-yl-1,1-dimethyl-ethyl amino)-1(S)-methyl-propoxy]-phenyl propionic acid hydrochloride 3-{2,3-dichloro-4-[2-(S)-hydroxy-3-(2-indan-2-yl-1,1-dimethyl-ethyl amino)-1(R)-methyl-propoxy]-phenyl propionic acid hydrochloride Each of the individual diastereomeric esters of Example 21 were saponified with aqueous NaOH and subsequently converted to the hydrochloric acid salt by treatment with hydrochloric acid in dry acetonitrile to provide the title compounds. Each individual diastereomeric acid possessed a molecular weight by mass spectral analysis which was consistent with the molecular formula: MS (ES) m/e 494 [M+H]+.

Example 23

Preparation of 3-{3-chloro-4-[(R)-2-hydroxy-3-(2-indan-2-yl-1,1-dimethyl-ethylamino)-propoxy]-phenyl}-propionic acid ethyl ester Following the general procedure of Example 1a-b except substituting 3-(3-chloro-4-hydroxy-phenyl)-propionic acid ethyl ester for bromo-2,3-difluorophenol the title compound was produced.

Example 24

Preparation of 3-{3-chloro-4-[(R)-2-hydroxy-3-(2-indan-2-yl-1,1-dimethyl-ethylamino)-propoxy]-phenyl}-propionic acid Following the general procedure of Example 1c except substituting the ester of Example 23 the title compound was produced.

Example 25

Preparation of 3-{3-bromo-4-[(R)-2-hydroxy-3-(2-indan-2-yl-1,1-dimethyl-ethylamino)-propoxy]-phenyl}-propionic acid ethyl ester Following the general procedure of Example 1a-b except substituting 3-(3-bromo-4-hydroxy-phenyl)-propionic acid ethyl ester for bromo-2,3-difluorophenol the title compound was produced.

Example 26

Preparation of 3-{3-chloro-4-[(R)-2-hydroxy-3-(2-indan-2-yl-1,1-dimethyl-ethylamino)-propoxy]-phenyl}-propionic acid Following the general procedure of Example 1c except substituting the ester of Example 25 the title compound was produced.

Example 27

Preparation of 3-{3-[(R)-2-hydroxy-3-(2-indan-2-yl-1,1-dimethyl-ethylamino)-propoxy]-phenyl}-propionic acid ethyl ester (a) 3-(3-hydroxy-phenyl)-propionic acid ethyl ester An ethanolic solution (250 mL) of 3-(3-Hydroxy-phenyl)-propionic acid (25 g, 100.4 mol) and concentrated sulfuric acid (3.0 mL) was heated to reflux for 2 hours and then at room temperature overnight. The solvent was removed by rotoevaporation, and the residue was brought up in ethyl acetate. The organic portion was washed successively with 5% $NaHCO_3$ (2×) and brine, dried over $MgSO_4$, filtered and concentrated to a brown oil (30 g, quant). this material was used without further purification.

(b) 3-[3-((R)-1-oxiranylmethoxy)-phenyl]-propionic acid ethyl ester

To an acetone solution (0.15 M, 170 mL) of 3-(3-Hydroxy-phenyl)-propionic acid ethyl ester (5.0 g, 25.77 mmol) was added K$_2$CO$_3$ (10.69 g, 77.32 mmol), and the mixture was heated to reflux for 30 min. After cooling this mixture to RT, (2R)-(−)-glycidyl 3-nitrobenzenesulfonate (6.68 g, 25.77 mmol) was added, and the resulting mixture was heated to reflux overnight. After cooling to room temperature, the solids were removed by filtration and washed well with ethyl acetate. The filtrate was concentrated and partitioned between ethyl acetate and 1N HCl. The organic portion was washed successively with 5% NaHCO$_3$ and brine, dried (MgSO$_4$), filtered and concentrated to a solid. Purification by FCC (30% ethyl acetate/hexanes) gave the product as a white solid in 93% yield (6.0 g). LCMS (m/z) M+H: 187

(c) 3-{3-[(R)-2-hydroxy-3-(2-indan-2-yl-1,1-dimethyl-ethylamino)-propoxy]-phenyl}-propionic acid ethyl ester An ethanolic solution (0.2 M, 100 mL) of the above-mentioned oxirane (5 g, 20.0 mmol) and 2-indan-2-yl-1,1-dimethyl-ethylamine (free base, 3.78 g, 20.0 mmol) was heated to reflux for 15 h. After solvent removal, the crude reaction mixture was purified by FCC (2% to 5% CH$_3$OH/CH$_2$Cl$_2$) to give the title compound as a yellow oil in 85% yield (7.5 g). LCMS (m/z) M+H: 440.

Example 28

Preparation of 3-{3-[(R)-2-hydroxy-3-(2-indan-2-yl-1,1-dimethyl-ethylamino)-propoxy]-phenyl}-propionic acid To a solution of 3-{3-[(R)-2-Hydroxy-3-(2-indan-2-yl-1,1-dimethyl-ethylamino)-propoxy]-phenyl}-propionic acid ethyl ester (1.3 g, 3.0 mmol) of Example 27 in ethanol (12 mL) and water (3 mL) was added 2N NaOH (3 mL, 6.0 mmol). The solution stirred at room temperature overnight. The ethanol was removed, and the residue was partitioned between diethyl ether and water. The aqueous portion was washed 3 times with diethyl ether and then adjusted to pH 5. The solid that precipitated from the aqueous layer was isolated by filtration to give the pure zwitterion as a white solid.

To an acetonitrile suspension of the zwitterion product was added 2M HCl in diethyl ether. The material briefly went into solution, and then precipitated as a white solid to give the title compound as the HCl salt, which was isolated by filtration and dried under vacuum (0.85 g, 63%). LCMS (m/z) M+H: 412.

Example 29

Preparation of 3-{4-[(R)-2-hydroxy-3-(2-indan-2-yl-1,1-dimethyl-ethylamino)-propoxy]-phenyl}-propionic acid The 25 mL round bottom flask was equipped with a magnetic stir bar, the dichloro propionic acid (0.12 g, 0.25 mmoles), 3 mL of absolute ethanol. To this was added 0.012 grams (10% w/w) of catalyst (Pd/C) and placed under hydrogen atmosphere. Stirring at room temperature till dechlorination complete. The reaction mixture was filtered through a pad of celite, washed with additional amount of ethanol and concentrated, purified by HPLC to yield TFA salt (36 mg). MS (ES) m/z 412 [M+H]$^+$ All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the area can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed:

1. A method of increasing serum parathyroid hormone levels in mammals, which comprises the administration to a subject in need of treatment thereof an effective amount of 3-{3,4-Difluoro-5-[(R)-2-hydroxy-3-(2-indan-2-yl-1,1-dimethyl-ethylamino)-propoxy]-phenyl}-propionic acid ethyl ester.

2. A method of increasing serum parathyroid hormone levels in mammals, which comprises the administration to a subject in need of treatment thereof an effective amount of a pharmaceutically acceptable salt of 3-{3,4-Difluoro-5-[(R)-2-hydroxy-3-(2-indan-2-yl-1,1-dimethyl-ethylamino)-propoxy]-phenyl}-propionic acid ethyl ester.

3. A method of increasing serum parathyroid hormone levels in mammals, which comprises the administration to a subject in need of treatment thereof an effective amount of 3-{3,4-Difluoro-5-[(R)-2-hydroxy-3-(2-indan-2-yl-1,1-dimethyl-ethylamino)-propoxy]-phenyl}-propionic acid ethyl ester hydrochloride.

* * * * *